United States Patent
Breton et al.

[11] Patent Number: 6,054,137
[45] Date of Patent: Apr. 25, 2000

[54] PROMOTING EPIDERMAL RENEWAL WITH PHLOROGLUCINOL

[75] Inventors: Lionel Breton, Versailles; Florence Girerd, Paris; Béatrice Renault, Saint Maurice, all of France

[73] Assignee: Societe L'Oreal S.A., Paris, France

[21] Appl. No.: 09/216,863

[22] Filed: Dec. 21, 1998

[30] Foreign Application Priority Data

Dec. 19, 1997 [FR] France ................... 97 16181

[51] Int. Cl.$^7$ .............. A61K 7/00; A61K 7/42; A61K 7/44
[52] U.S. Cl. .............. 424/400; 424/59; 424/60; 424/401; 514/937; 514/938; 514/944; 514/945
[58] Field of Search .................. 424/400, 401, 424/59, 60; 514/937, 938, 944, 945

[56] References Cited

U.S. PATENT DOCUMENTS

| | | | |
|---|---|---|---|
| 5,093,109 | 3/1992 | Mausner | 424/63 |
| 5,536,500 | 7/1996 | Galey et al. | 424/401 |
| 5,952,373 | 9/1999 | Lazendorfer et al. | 514/456 |

FOREIGN PATENT DOCUMENTS

| | | |
|---|---|---|
| 0 103 878 | 9/1983 | European Pat. Off. . |
| 0 451 889 A1 | 10/1991 | European Pat. Off. . |
| 2 315 908 | 7/1976 | France . |
| 1269573 | 7/1991 | France . |
| 55-115814 | 9/1980 | Japan . |
| 57-31606 | 2/1982 | Japan . |
| 57-167921 | 10/1982 | Japan . |
| 63-277615 | 11/1988 | Japan . |
| 64-13018 | 1/1989 | Japan . |
| 4-202138 | 7/1992 | Japan . |
| 4-235112 | 8/1992 | Japan . |
| 5-27005 | 2/1993 | Japan . |
| 5-78230 | 3/1993 | Japan . |
| 5-105621 | 4/1993 | Japan . |
| 5-105643 | 4/1993 | Japan . |
| 5-125390 | 5/1993 | Japan . |
| 5-221845 | 8/1993 | Japan . |
| 5-310526 | 11/1993 | Japan . |
| 6-92835 | 4/1994 | Japan . |
| 6-312924 | 11/1994 | Japan . |
| 6-321754 | 11/1994 | Japan . |
| 7-259452 | 10/1995 | Japan . |
| 7-300469 | 11/1995 | Japan . |
| 8-12664 | 1/1996 | Japan . |
| 8-259421 | 10/1996 | Japan . |
| 9-124474 | 5/1997 | Japan . |
| 9-132527 | 5/1997 | Japan . |
| 10-306009 | 11/1998 | Japan . |
| 10-306011 | 11/1998 | Japan . |
| 11-246333 | 9/1999 | Japan . |
| WO 92/07544 | 5/1992 | WIPO . |
| WO 99/32078 | 7/1999 | WIPO . |

OTHER PUBLICATIONS

English abstract of Japanese 6–312924 Nov. 8, 1994.
English abstract of Japanese 4–202138 Jul. 22, 1992.
English abstract of Japanese 4–235112 Aug. 24, 1992.
English abstract of Japanese 5–125390 May 21, 1993.
English abstract of Japanese 6–92835 Apr. 5, 1994.
English abstract of Japanese 55–115814 Sep. 6, 1980.
English abstract of EP 0103878 Sep. 17, 1983.
French description of Japanese 63–277615 Nov. 15, 1988.
English abstract of Japanese 5–221845 Aug. 31, 1993.
English abstract of EP 0506961 Oct. 7, 1992.
English abstract of Japanese 5310526 Nov. 22, 1993.
English abstract of Japanese 1013018 Jan. 17, 1989.
English abstract of Japanese 5–78230 Mar. 30, 1993.
English abstract of Japanese 5–105621 Apr. 27, 1993.
English abstract of Japanese 5–105643 Apr. 27, 1993.
English abstract of Japanese 6–321754 Nov. 22, 1994.
English abstract of Japanese 9–124474 May 13, 1997.
English abstract of Japanese 9–132527 May 20, 1997.
English abstract of Japanese 10–306011 Nov. 17, 1998.
English abstract of Japanese 10–306009 Nov. 17, 1998.

*Primary Examiner*—Shelley A. Dodson
*Attorney, Agent, or Firm*—Burns, Doane, Swecker & Mathis, L.L.P.

[57] ABSTRACT

The subject-matter of the invention is a cosmetic composition comprising, in a cosmetically acceptable medium, at least phloroglucinol or one of its derivatives. Another subject-matter of the invention is the use of phloroglucinol or of its derivatives in a cosmetic composition intended to promote epidermal renewal.

22 Claims, No Drawings

PROMOTING EPIDERMAL RENEWAL WITH PHLOROGLUCINOL

This application claims priority under 35 U.S.C. §§119 and/or 365 to patent application Ser. No. 97-16181 filed in France on Dec. 19, 1997; the entire content of which is hereby incorporated by reference.

BACKGROUND OF THE INVENTION

1. Technical Field of the Invention

The subject-matter of the invention is a cosmetic composition comprising, in a cosmetically acceptable medium, at least phloroglucinol or one of its derivatives.

Another subject-matter of the invention is the use of phloroglucinol or its derivatives in a cosmetic composition intended to promote epidermal renewal.

2. Description of Prior Art

The skin constitutes a physical barrier between the body and its environment. It is composed of two tissues, the epidermis and the dermis.

The dermis provides the epidermis with a solid backing. It is also its nutrient component. It is mainly composed of fibroblasts and of an extracellular matrix itself composed mainly of collagen, elastin and a so-called fundamental substance, these components being synthesized by the fibroblast. Leucocytes, mastocytes or even tissue macrophages are also found therein. It also contains blood vessels and nerve fibres.

The epidermis is a desquamating multilayered epithelium with an average thickness of 100 µm and is conventionally divided into a basal layer of keratinocytes, which constitutes the germinal layer of the epidermis, a so-called prickle cell layer, composed of several layers of polyhedral cells positioned on the germinal cells, a so-called granular layer, composed of flattened cells comprising distinct cytoplasmic inclusions, keratohyalin granules, and finally an upper layer, known as the horny layer (or stratum corneum), composed of keratinocytes at the terminal stage of their differentiation, known as corneocytes. The latter are anucleate mummified cells which derive from keratinocytes. The stacking of these corneocytes constitutes the horny layer which is responsible, inter alia, for the barrier function of the epidermis.

Epidermal differentiation follows a continuous and controlled maturing process in which the basal keratinocytes are converted while migrating, in order to result in the formation of corneocytes, dead cells which are completely keratinized. This differentiation is the consequence of perfectly coordinated phenomena which will result in the maintenance of a constant thickness and thus ensure the homeostasis of the epidermis. This involves regulating the number of cells which take part in the differentiation process and the number of cells which desquamate.

During the normal desquamation process, only the corneocytes closest to the surface detach from the surface of the epidermis.

It is known that, during chronobiological ageing, the thickness of the epidermis is reduced. The cell divisions of the basal layer decrease in number. The renewal time of the horny cells lengthens. The maturing of these cells is incomplete and the keratinization no longer results in the creation of an even and homogeneous horny layer.

It is also known that prolonged and/or repeated exposure to the sun produces fairly similar results on the epidermis. This is photoinduced ageing. It is also known that, in the case of certain diseases, such as ichthyosis, the skin is subjected to damage due to lack of cell proliferation.

It is also known that, at the menopause, cutaneous ageing accelerates, the thickness of the skin decreases and women complain that their skin feels tight and that it takes on the look of a "dry skin", indeed of the appearance of xerosis. It is known that hormonal deficiencies associated with the menopause are accompanied by a general slowing down of the cell metabolism, from which it might all the same be supposed that the effects which women experience are related in particular to a decrease in the proliferation of keratinocytes.

The need to have available a means for facilitating cell multiplication, in particular the multiplication of the cells of the epidermis, is then understood. This is because such means make it possible to facilitate the regeneration of the epidermis and to restore a youthful appearance to the skin.

How such products could be useful in the case of cicatrization is also assessed.

SUMMARY OF THE INVENTION

The applicant have has now discovered, surprisingly and unexpectedly, that phloroglucinol or its derivatives have the property of inducing the proliferation of normal human keratinocytes.

Phloroglucinol or 1,3,5-trihydroxybenzene corresponds to the formula:

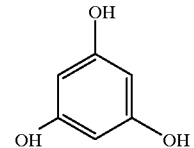

It is present, for example, in plant extracts, such as, for example, those of *Eucalyptus kino* or of *Acacia arabica*.

Phloroglucinol derivatives are understood to mean those mentioned in "Dictionary of Natural Products on CD-ROM" (Chapman and Hall (1997), London), such as 1,3,5-trimethoxybenzene, 1,3,5-triethoxybenzene, 3,5-dimethoxyphenol or taxicatigenin, 5-methoxy-1,3-benzenediol or flamenol, 3-hydroxy-5-methoxyphenol, 1,3,5-triphenoxybenzene, tribenzyl O-β-glucopyranoside or phlorin, or taxicatin or dimethoxyphenyl O-β-glucopyranoside, or those mentioned in "The organic constituents of higher plants (T. Robinson, 1983, Corduss Press, North Amerst), such as the tautomers of phloroglucinol (cyclic triketones), desaspidin, lupulon, humulon, ceroptene, felicitin, leptospermone, eugenone, hulupon, aspidinol, α-kosin, tasmanone or angustione.

These derivatives are present in a great variety of plants and can be extracted therefrom by conventional methods. Mention will be made, for example, of the plants of the family of Pteridaceae (Asnidium), Cannabinaceae (*Humulus lupulus*) or Myrtaceae (*Eugenia caryophyllata, Eucalyptus risdoni*).

DETAILED DESCRIPTION OF BEST MODE AND SPECIFIC/PREFERRED EMBODIMENTS OF THE INVENTION

In the prior art, phloroglucinol or its derivatives are known as inhibitors of the photosynthetic transportation of electrons, as inhibitor of tumour promotion, as inhibitors of photophosphorylation or as inhibitor of the metabolism of arachidonic acid. They are also antihelmintics, antispasmodic agents, insecticides, bactericides or in particular colorants, particularly used for dyeing tissues.

To the knowledge of the applicant have, it has never been disclosed in the state of the art that phloroglucinol or its derivatives stimulates the proliferation of keratinocytes.

The subject-matter of the invention is thus a cosmetic composition comprising, in a cosmetically acceptable medium, an effective amount of phloroglucinol or of at least one of its derivatives.

According to the invention, phloroglucinol or its derivatives can be of natural or synthetic origin. Natural origin is understood to mean phloroglucinol or its derivatives prepared from plant material in which they are present in the natural state. Synthetic origin is understood to mean phloroglucinol or its derivatives prepared by chemical synthesis or by biotechnology. Thus, subsequently in the text, the term phloroglucinol is understood as denoting purified phloroglucinol or its purified derivatives of natural or synthetic origin or any preparation comprising them.

Phloroglucinol or 1,3,5-trimethoxybenzene is preferably used according to the invention.

Of course, it is possible according to the invention to use phloroglucinol or its derivatives alone or as a mixture.

It has been seen above that, during chronobiological and/or photoinduced ageing, the size of the epidermis decreased mainly under the effect of a reduction in the number of cell divisions in the basal layer and of a lengthening in the renewal time of the horny cells.

Thus, one of the aspects of the invention is therefore to provide a cosmetic composition intended to stimulate the proliferation of keratinocytes of the skin comprising, in a cosmetically acceptable medium, an effective amount of phloroglucinol or of one of its derivatives.

Another subject-matter of the invention is a cosmetic composition intended to combat chronobiological and/or photoinduced ageing comprising, in a cosmetically acceptable medium, an effective amount of phloroglucinol or of one of its derivatives.

A further subject-matter of the invention is a cosmetic composition intended to stimulate cicatrization comprising, in a cosmetically acceptable medium, an effective amount of phloroglucinol or of one of its derivatives.

Finally, a subject-matter of the invention is a cosmetic composition intended to combat the cutaneous effects of the menopause comprising, in a cosmetically acceptable medium, an effective amount of phloroglucinol or of one of its derivatives.

Cosmetically acceptable medium is understood to mean a medium compatible with the skin, the scalp, the mucous membranes, the nails and the hair.

The amount of phloroglucinol which can be used according to the invention very clearly depends on the desired effect and must be an amount thereof which is effective for stimulating the proliferation of keratinocytes.

By way of example, the amount of phloroglucinol or of its derivatives which can be used according to the invention can range, for example, from 0.0001% to 5% and preferably from 0.001% to 2% of the total weight of the composition.

As the skin is composed of many components other than keratinocytes, it proves to be advantageous, when phloroglucinol or one of its derivatives according to the invention is used, to promote at the same time the synthesis of these other components, such as, for example, collagen and/or lipids.

Thus, a subject-matter of the invention is a cosmetic composition comprising, in a cosmetically acceptable medium, phloroglucinol or one of its derivatives and at least one other product which stimulates the synthesis of collagen and/or the synthesis of lipids.

In this respect, mention may be made, as product which stimulates the synthesis of collagen and/or the synthesis of lipids, of plant hormones, such as auxins, or compounds of plant origin, such as cinnamic acid.

Thus, the compositions according to the invention can comprise, in addition to phloroglucinol or to one of its derivatives, cinnamic acid or its derivatives and/or a plant hormone, particularly an auxin chosen from indoleacetic acid (IAA), 4-chloro-indole-3-acetic acid (4-Cl-IAA), phenylacetic acid (PAA), indole-3-butyric acid (IBA), 2,4-dichloro-phenoxyacetic acid (2,4-D), α-naphthaleneacetic acid (α-NAA), β-naphthoxyacetic acid, indoleethanol, indoleacetaldehyde and indoleacetonitrile.

Preferably, according to the invention, the composition comprises phloroglucinol or one of its derivatives and cinnamic acid and/or β-naphthoxyacetic acid.

Mention may also be made, as product which stimulates the synthesis of collagen, of vitamin C and its derivatives.

In the compositions according to the invention, the product which stimulates the synthesis of lipids and/or of collagen can be an amount thereof of between 10–6% and 10% and preferably between 10–3% and 5% of the total weight of the composition.

In addition, a subject-matter of the invention is the use, in a cosmetic composition, of an effective amount of phloroglucinol or of its derivatives, the phloroglucinol or the composition being intended to stimulate the proliferation of keratinocytes and thus to promote the regeneration of the skin.

Likewise, one of the aspects of the invention is to provide for the use, in a cosmetic composition, of an effective amount of phloroglucinol or of its derivatives, the phloroglucinol or the composition being intended to combat chronobiological and/or photoinduced ageing.

Under yet another aspect, a subject-matter of the invention is the use, in a cosmetic composition, of an effective amount of phloroglucinol or of its derivatives, the phloroglucinol or the composition being intended to promote cicatrization.

Under yet another aspect, a subject-matter of the invention is the use, in a cosmetic composition, of an effective amount of phloroglucinol or of its derivatives, the phloroglucinol or the composition being intended to combat the cutaneous effects of the menopause, particularly the effects of the menopause on the proliferation of keratinocytes.

The composition according to the invention very obviously comprises a cosmetically acceptable vehicle and can be provided in all the pharmaceutical dosage forms normally used for a topical application, in particular in the form of an aqueous, aqueous/alcoholic or oily solution, of an oil-in-water or water-in-oil or multiple emulsion, of an aqueous or oily gel, of a solid, pasty or liquid anhydrous product, or of a dispersion of oil in an aqueous phase using spherules, it being possible for these spherules to be polymeric nanoparticles, such as nanospheres and nanocapsules, or, better still, lipid vesicles of ionic and/or non-ionic type.

This composition can be more or less fluid and have the appearance of a white or coloured cream, of an ointment, of a milk, of a lotion, of a serum, of a paste or of a foam. It can optionally be applied to the skin in aerosol form. It can also be provided in solid form, for example in stick form. It can be used as care product, as cleansing product, as make-up product or even as simple deodorant product.

In a known way, the composition of the invention can also contain adjuvants usual in the cosmetic and dermatological fields, such as hydrophilic or lipophilic gelling agents, hydrophilic or lipophilic active principles, preservatives, antioxidants, solvents, fragrances, fillers, screening agents, pigments, chelating agents, odour absorbers and colouring materials. The amounts of these various adjuvants are those conventionally used in the fields under consideration, for example from 0.01% to 20% of the total weight of the composition. These adjuvants, according to their nature, can be introduced in the fatty phase, in the aqueous phase, in the lipid vesicles and/or in the nanoparticles.

When the composition of the invention is an emulsion, the proportion of the fatty phase can range from 5% to 80% by weight and preferably from 5% to 50% of the total weight of the composition. The oils, the emulsifiers and the coemulsifiers used in the composition in the emulsion form are chosen from those conventionally used in the field under consideration. The emulsifier and the coemulsifier are present in the composition in a proportion ranging from 0.3% to 30% by weight and preferably from 0.5% to 20% of the total weight of the composition.

Mention may be made, as oils which can be used in the invention, of mineral oils, oils of plant origin (apricot oil, sunflower oil), oils of animal origin, synthetic oils, silicone oils and fluorinated oils (perfluoropolyethers). Use may also be made, as fatty substances, of fatty alcohols (cetyl alcohol), fatty acids or waxes (beeswax).

Mention may be made, as emulsifiers and coemulsifiers which can be used in the invention, of, for example, polyethylene glycol fatty acid esters, such as PEG-40 stearate or PEG-100 stearate, or polyol fatty acid esters, such as glyceryl stearate and sorbitan tristearate.

Mention may in particular be made, as hydrophilic gelling agents, of carboxyvinyl polymers (carbomer), acrylic copolymers, such as acrylate/alkyl acrylate copolymers, polyacrylamides, polysaccharides, natural gums and clays and mention may be made, as lipophilic gelling agents, of modified clays, such as bentones, metal salts of fatty acids, hydrophobic silica and polyethylenes.

The composition can contain other hydrophilic active principles, such as proteins or protein hydrolysates, amino acids, polyols, urea, allantoin, sugars and sugar derivatives, water-soluble vitamins, plant extracts and hydroxyacids.

Use may be made, as lipophilic active principles, of retinol (vitamin A) and its derivatives, tocopherol (vitamin E) and its derivatives, essential fatty acids, ceramides, essential oils or salicylic acid and its derivatives.

It is also possible to use according to the invention, in combination with phloroglucinol or one of its derivatives, compounds chosen from:

plant hormones;

antibacterial agents, such as macrolides, pyranosides and tetracyclines and in particular erythromycin;

calcium antagonist agents, such as verapamil and diltiazem;

OH radical scavengers, such as dimethyl sulphoxide;

plant extracts, such as those of Iridaceae or of soybean, extracts which can then contain, or otherwise, isoflavones;

microorganism extracts, including in particular bacterial extracts, such as those of non-photosynthetic filamentary bacteria.

Other compounds can also be added to the above list, namely, for example, potassium channel openers, such as diazoxide and minoxidil, spiroxazone, phospholipids, such as lecithin, linoleic and linolenic acids, salicylic acid and its derivatives disclosed in French Patent FR 2,581,542, such as the salicylic acid derivatives carrying an alkanoyl group having from 2 to 12 carbon atoms at the 5 position of the benzene ring, hydroxycarboxylic or ketocarboxylic acids and their corresponding esters, lactones and salts, anthralin, carotenoids, eicosatetraenoic and eicosatrienoic acids or their esters and amides, or vitamin D and its derivatives.

According to the invention, it is possible, inter alia, to combine phloroglucinol or one of its derivatives with other active agents intended in particular for the prevention and/or treatment of cutaneous disorders. Mention may be made, among these active agents, of, by way of example:

agents which modulate cutaneous pigmentation and/or proliferation and/or differentiation, such as retinoic acid and its isomers, retinol and its esters, vitamin D and its derivatives, oestrogens, such as oestradiol, kojic acid or hydroquinone;

agents which modulate bacterial adhesion to the skin and/or mucous membranes, such as honey, in particular acacia honey, and certain sugar derivatives;

agents for combating parasites, in particular metronidazole, crotamiton or pyrethroids;

antifungals, in particular compounds belonging to the imidazole class, such as econazole, ketoconazole or miconazole or their salts, polyene compounds, such as amphotericin B, compounds of the allylamine family, such as terbinafine, or alternatively octopirox;

antiviral agents, such as acyclovir;

steroidal anti-inflammatory agents, such as hydrocortisone, betamethasone valerate or clobetasol propionate, or non-steroidal anti-inflammatory agents, such as ibuprofen and its salts, diclofenac and its salts, acetylsalicylic acid, acetaminophen or glycyrrhetinic acid;

anaesthetic agents, such as lidocaine hydrochloride and its derivatives;

antipruriginous agents, such as thenaldine, trimeprazine or cyproheptadine;

keratolytic agents, such as α- and β-hydroxycarboxylic acids or β-ketocarboxylic acids, their salts, amides or esters and more particularly hydroxyacids, such as glycolic acid, lactic acid, salicylic acid, citric acid and generally fruit acids, and 5-(n-octanoyl)salicylic acid;

agents for combating free radicals, such as α-tocopherol or its esters, superoxide dismutases, certain metal chelating agents or ascorbic acid and its esters;

antiseborrhoeics, such as progesterone;

antidandruff agents, such as octopirox or zinc pyrithione;

antiacne agents, such as retinoic acid or benzoyl peroxide, substances such as substance P, CGRP or bradykinin antagonists or NO-synthase inhibitors, compounds described as being active in the treatment of sensitive skin and as exhibiting anti-irritant effects, in particular with respect to irritant compounds possibly present in the compositions.

Thus, another subject-matter of the invention relates to a composition comprising an effective amount of phloroglucinol or of one of its derivatives and at least one agent chosen from antibacterial agents, agents for combating parasites, antifungals, antiviral agents, anti-inflammatory agents, antipruriginous agents, anaesthetic agents, keratolytic agents, agents for combating free radicals, antiseborrhoeics, antidandruff agents, antiacne agents, agents which modulate cutaneous pigmentation and/or proliferation and/or differentiation, substance P, CGRP or bradykinin antagonists or NO-synthase inhibitors.

Use may in particular be made, as active principles, of moisturizing agents, such as polyols (for example glycerol), vitamins (for example D-panthenol), anti-inflammatory agents, soothing agents (allantoin, cornflower water), UVA and UVB screening agents, mattifying agents (for example the partially crosslinked polydimethylorganosiloxanes sold under the name KSG® by Shin Etsu), and their mixtures.

It is also possible to add anti-wrinkle active principles and in particular tensioning products, such as plant proteins and their hydrolysates, in particular the soya proteins extract sold under the name of Eleseryl® by the company LSN or the oats derivative sold under the name Reductine® by the company Silab.

Of course, phloroglucinol or one of its derivatives can be used in the preparation of cosmetic and/or pharmaceutical compositions, particularly dermatological compositions, intended to stimulate the proliferation of keratinocytes.

Other characteristics and advantages of the invention will emerge more clearly from the examples which follow, given by way of illustration and without implied limitation. In what follows or what precedes, the proportions are given as percentage by weight, except when otherwise indicated.

EXAMPLE 1

Study of the effect of 1,3,5-trimethoxybenzene on the proliferation of normal human keratinocytes cultured as a monolayer:

Equipment and methods:

Cells

The products are tested on 2nd passage normal human keratinocytes cultured in KGM medium (serum-free defined medium sold by the company Clonetics). The range of concentrations is between $10^{-4}$M and $10^{-7}$M. The products are tested twice on 2 different plates.

Control 250 ng/ml epinephrine is employed as positive control of the proliferation.

Dissolution of the product:

The products are dissolved in dimethyl sulphoxide (DMSO). A $1 \times 10^{-2}$M mother solution is prepared in DMSO. The following dilutions are carried out in KGM.

The keratinocytes are seeded at 6000 cells/cm². After culturing for 24 h, the product is applied to the cells for 72 h. The medium is replaced after treatment for 48 h.

BrdU Test:

BrdU kit (Boehringer Mannheim).

On the second day of treatment, a thymidine analogue (BrdU) is added to the culture medium overnight. This analogue makes it possible to label the cells during DNA synthesis. On the third day of treatment, the cells which have incorporated BrdU are identified with an anti-BrdU antibody.

Alamar Blue Test:

Alamar Blue measures the metabolic activity of the cells. The metabolic activity of the cells leads to the reduction of the culture medium, which is reflected by the change in the latter from blue to pink.

On the third day of the treatment, the cells are brought into contact with the Alamar Blue diluted to 1/10 in KGM. The cells are incubated for 6 h and the optical density (O.D.) is performed directly on the culture supernatant.

Results:

For each product, the score (see table) is attributed as a function of the result obtained with respect to epinephrine (positive control for the proliferation).

| OD value | Score attributed |
|---|---|
| Product > Epinephrine | 3 |
| Product = Epinephrine | 2 |
| Product < Epinephrine but > Control culture | 1 |
| Product = Control culture | 0 |
| Product < Control culture | −1 |

1) Cytotoxicity of the products (Test with Alamar Blue) From $10^{-5}$M to $10^{-7}$M, no pronounced cytotoxic effect is observed.

2) Proliferative effect of 1,3,5-trimethoxybenzene: 1,3,5-Trimethoxybenzene induces proliferation of the keratinocytes at $10^{-5}$M.

Conclusion: Phloroglucinol induces the proliferation of normal human keratinocytes as a monolayer with a score of 1.

EXAMPLE 2

Examples of compositions according to the invention. These compositions are obtained by conventional techniques commonly used in cosmetics or in pharmaceuticals.

| Composition No. 1 | |
|---|---|
| Beeswax | 1.5% |
| Apricot kernel oil | 13.0% |
| Preservatives | 0.3% |
| Fragrance | 0.4% |
| Trimethoxybenzene | 0.01% |
| Xanthan | 0.5% |
| Cyclopentadimethylsiloxane | 5.0% |
| Sterilized demineralized water | 69.29% |
| Sucrose mono- and dipalmitate/stearate | 3.0% |
| Methylglucose sesquistearate | 3.0% |
| Stearic acid | 1.0% |
| Cetyl alcohol | 3.0% |
| Composition No. 2 | |
| Beeswax | 1.5% |
| Apricot kernel oil | 13.0% |
| Preservatives | 0.3% |
| Fragrance | 0.4% |
| Trimethoxybenzene | 0.01% |
| Cinnamic acid | 0.01% |
| Xanthan | 0.5% |
| Cyclopentadimethylsiloxane | 5.0% |
| Sterilized demineralized water | 69.28% |
| Sucrose mono- and dipalmitate/stearate | 3.0% |
| Methylglucose sesquistearate | 3.0% |
| Stearic acid | 1.0% |
| Cetyl alcohol | 3.0% |
| Composition No. 3 | |
| Beeswax | 1.5% |
| Apricot kernel oil | 13.0% |
| Preservatives | 0.3% |
| Fragrance | 0.4% |
| Trimethoxybenzene | 0.01% |
| Cinnamic acid | 0.01% |
| β-Naphthoxyacetic acid | 0.01% |
| Xanthan | 0.5% |
| Cyclopentadimethylsiloxane | 5.0% |
| Sterilized demineralized water | 69.27% |
| Sucrose mono- and dipalmitate/stearate | 3.0% |
| Methylglucose sesquistearate | 3.0% |
| Stearic acid | 1.0% |
| Cetyl alcohol | 3.0% |
| Composition No. 4 | |
| Beeswax | 1.5% |
| Apricot kernel oil | 13.0% |

Composition No. 1

| | |
|---|---|
| Preservatives | 0.3% |
| Fragrance | 0.4% |
| Phloroglucinol | 0.01% |
| Xanthan | 0.5% |
| Cyclopentadimethylsiloxane | 5.0% |
| Sterilized demineralized water | 69.29% |
| Sucrose mono- and dipalmitate/stearate | 3.0% |
| Methylglucose sesquistearate | 3.0% |
| Stearic acid | 1.0% |
| Cetyl alcohol | 3.0% |

Composition No. 5

| | |
|---|---|
| Beeswax | 1.5% |
| Apricot kernel oil | 13.0% |
| Preservatives | 0.3% |
| Fragrance | 0.4% |
| Phloroglucinol | 0.01% |
| Cinnamic acid | 0.01% |
| Xanthan | 0.5% |
| Cyclopentadimethylsiloxane | 5.0% |
| Sterilized demineralized water | 69.28% |
| Sucrose mono- and dipalmitate/stearate | 3.0% |
| Methylglucose sesquistearate | 3.0% |
| Stearic acid | 1.0% |
| Cetyl alcohol | 3.0% |

Composition No. 6

| | |
|---|---|
| Beeswax | 1.5% |
| Apricot kernel oil | 13.0% |
| Preservatives | 0.3% |
| Fragrance | 0.4% |
| Phloroglucinol | 0.01% |
| Cinnamic acid | 0.01% |
| β-Naphthoxyacetic acid | 0.01% |
| Xanthan | 0.5% |
| Cyclopentadimethylsiloxane | 5.0% |
| Sterilized demineralized water | 69.27% |
| Sucrose mono- and dipalmitate/stearate | 3.0% |
| Methylglucose sesquistearate | 3.0% |
| Stearic acid | 1.0% |
| Cetyl alcohol | 3.0% |

Composition No. 7

| | |
|---|---|
| Beeswax | 1.5% |
| Apricot kernel oil | 13.0% |
| Preservatives | 0.3% |
| Fragrance | 0.4% |
| Leptospermone | 0.01% |
| Cinnamic acid | 0.01% |
| β-Naphthoxyacetic acid | 0.01% |
| Xanthan | 0.5% |
| Cyclopentadimethylsiloxane | 5.0% |
| Sterilized demineralized water | 69.27% |
| Sucrose mono- and dipalmitate/stearate | 3.0% |
| Methylglucose sesquistearate | 3.0% |
| Stearic acid | 1.0% |
| Cetyl alcohol | 3.0% |

Composition No. 8

| | |
|---|---|
| Beeswax | 1.5% |
| Apricot kernel oil | 13.0% |
| Preservatives | 0.3% |
| Fragrance | 0.4% |
| Eugenone | 0.01% |
| Cinnamic acid | 0.01% |
| β-Naphthoxyacetic acid | 0.01% |
| Xanthan | 0.5% |
| Cyclopentadimethylsiloxane | 5.0% |
| Sterilized demineralized water | 69.27% |
| Sucrose mono- and dipalmitate/stearate | 3.0% |
| Methylglucose sesquistearate | 3.0% |
| Stearic acid | 1.0% |
| Cetyl alcohol | 3.0% |

Composition No. 9

| | |
|---|---|
| Beeswax | 1.5% |
| Apricot kernel oil | 13.0% |
| Preservatives | 0.3% |
| Fragrance | 0.4% |
| Humulon | 0.01% |
| Cinnamic acid | 0.01% |
| β-Naphthoxyacetic acid | 0.01% |
| Xanthan | 0.5% |
| Cyclopentadimethylsiloxane | 5.0% |
| Sterilized demineralized water | 69.27% |
| Sucrose mono- and dipalmitate/stearate | 3.0% |
| Methylglucose sesquistearate | 3.0% |
| Stearic acid | 1.0% |
| Cetyl alcohol | 3.0% |

Composition No. 10

| | |
|---|---|
| Beeswax | 1.5% |
| Apricot kernel oil | 13.0% |
| Preservatives | 0.3% |
| Fragrance | 0.4% |
| Hulupon | 0.01% |
| Cinnamic acid | 0.01% |
| β-Naphthoxyacetic acid | 0.01% |
| Xanthan | 0.5% |
| Cyclopentadimethylsiloxane | 5.0% |
| Sterilized demineralized water | 69.27% |
| Sucrose mono- and dipalmitate/stearate | 3.0% |
| Methylglucose sesquistearate | 3.0% |
| Stearic acid | 1.0% |
| Cetyl alcohol | 3.0% |

Composition No. 11

| | |
|---|---|
| Beeswax | 1.5% |
| Apricot kernel oil | 13.0% |
| Preservatives | 0.3% |
| Fragrance | 0.4% |
| Ceroptene | 0.01% |
| Cinnamic acid | 0.01% |
| β-Naphthoxyacetic acid | 0.01% |
| Xanthan | 0.5% |
| Cyclopentadimethylsiloxane | 5.0% |
| Sterilized demineralized water | 68.77% |
| Sucrose mono- and dipalmitate/stearate | 3.0% |
| Methylglucose sesquistearate | 3.0% |
| Stearic acid | 1.0% |
| Cetyl alcohol | 3.0% |
| Soybean extract | 0.5% |

Composition No. 12

| | |
|---|---|
| Beeswax | 1.5% |
| Apricot kernel oil | 13.0% |
| Preservatives | 0.3% |
| Fragrance | 0.4% |
| Aspidinol | 0.01% |
| Cinnamic acid | 0.01% |
| β-Naphthoxyacetic acid | 0.01% |
| Xanthan | 0.5% |
| Cyclopentadimethylsiloxane | 5.0% |
| Sterilized demineralized water | 69.27% |
| Sucrose mono- and dipalmitate/stearate | 3.0% |
| Methylglucose sesquistearate | 3.0% |
| Stearic acid | 1.0% |
| Cetyl alcohol | 3.0% |

Composition No. 13

| | |
|---|---|
| Beeswax | 1.5% |
| Apricot kernel oil | 13.0% |
| Preservatives | 0.3% |
| Fragrance | 0.4% |
| Tasmanone | 0.01% |
| Cinnamic acid | 0.01% |
| β-Naphthoxyacetic acid | 0.01% |
| Xanthan | 0.5% |
| Cyclopentadimethylsiloxane | 5.0% |
| Sterilized demineralized water | 69.27% |
| Sucrose mono- and dipalmitate/stearate | 3.0% |
| Methylglucose sesquistearate | 3.0% |
| Stearic acid | 1.0% |
| Cetyl alcohol | 3.0% |

-continued

Composition No. 1

Composition No. 14

| | |
|---|---|
| Beeswax | 1.5% |
| Apricot kernel oil | 13.0% |
| Preservatives | 0.3% |
| Fragrance | 0.4% |
| Angustione | 0.01% |
| Cinnamic acid | 0.01% |
| β-Naphthoxyacetic acid | 0.01% |
| Xanthan | 0.5% |
| Cyclopentadimethylsiloxane | 5.0% |
| Sterilized demineralized water | 69.27% |
| Sucrose mono- and dipalmitate/stearate | 3.0% |
| Methylglucose sesquistearate | 3.0% |
| Stearic acid | 1.0% |
| Cetyl alcohol | 3.0% |

We claim:

1. A regime/regimen for promoting epidermal renewal and stimulating proliferation of human keratinocytes, comprising administering to a candidate individual in need of such treatment, for such period of time as required to elicit the desired therapeutic response, a thus-effective amount of phloroglucinol or of at least one derivative thereof.

2. A regime/regimen for combating chronobiological and/or photoinduced aging of human skin, comprising administering to a candidate individual in need of such treatment, for such period of time as required to elicit the desired therapeutic response, a thus-effective amount of phloroglucinol or of at least one derivative thereof.

3. A regime/regimen for promoting cicatrization on human skin, comprising administering to a candidate individual in need of such treatment, for such period of time as required to elicit the desired therapeutic response, a thus-effective amount of phloroglucinol or of at least one derivative thereof.

4. A regime/regime for combating the objectionable cutaneous effects of menopause, comprising administering to a candidate individual in need of such treatment, for such period of time as required to elicit the desired therapeutic response, a thus-effective amount of phloroglucinol or of at least one derivative thereof.

5. The regime/regimen as defined by claim 1, 2, 3 or 4, comprising administering to a candidate individual in need of such treatment, for such period of time as required to elicit the desired therapeutic response, a thus-effective amount of at least one phloroglucinol derivative selected from among 1,3,5-trimethoxybenzene, 3,5-dimethoxyphenol, taxicatigenin, 5-methoxy-1,3-benzenediol, flamenol, 3-hydroxy-5-methoxyphenol, 1,3,-triphenoxybenzene, tribenzyl O-β-glucopyranoside, phlorin, taxicatin, dimethoxyphenyl O-β-glucopyranoside, a tautomer of phloroglucinol (cyclic triketone), desaspidin, lupulon, humulon, ceroptene, felicitin, leptospermone, eugenone, hulupon, aspidinol, α-kosin, tasmanone and angustione.

6. The regime/regimen as defined by claim 5, comprising administering to a candidate individual in need of such treatment, for such period of time as required to elicit the desired therapeutic response, a thus-effective amount of phloroglucinol or 1,3,5-trimethoxybenzene.

7. The regime/regimen as defined by claim 1, 2, 3 or 4, comprising topically applying onto the skin of a candidate individual in need of such treatment, for such period of time as required to elicit the desired therapeutic response, a thus-effective amount of phloroglucinol or of at least one derivative thereof.

8. The regime/regimen as defined by claim 1, 2, 3 or 4, comprising coadministering to said candidate individual, an effective amount of at least one active species which stimulates the synthesis of collagen and/or the synthesis of lipids.

9. The regime/regimen as defined by claim 8, said at least one active species comprising one of plant origin.

10. The regime/regimen as defined by claim 9, said at least one active species comprising a plant hormone auxin, or plant compound.

11. The regime/regimen as defined by claim 10, said at least one active species being selected from among cinnamic acid or derivative thereof, indoleacetic acid (IAA), 4-chloroindole-3-acetic acid (4-C1-IAA), phenylacetic acid (PAA), indole-3-butyric acid (IBA), 2,4-dichlorophenoxyacetic acid (2,4-D), α-naphthaleneacetic acid (α-NAA), β-naphthoxyacetic acid, indoleethanol, indoleacetaldehyde and indoleacetonitrile.

12. The regime/regimen as defined by claim 11, said at least one active species comprising cinnamic acid and/or β-naphthoxyacetic acid.

13. The regime/regimen as defined by claim 8, said at least one active species comprising vitamin C or derivative thereof.

14. A cosmetic/dermatological composition suited for promoting epidermal renewal and stimulating proliferation of human keratinocytes, for combating chronobiological and/or photoinduced aging of human skin, for promoting cicatrization on human skin, or for combating the objectionable cutaneous effects of menopause, comprising a thus-effective amount of phloroglucinol or of at least one derivative thereof, formulated into a topically applicable, cosmetically acceptable medium therefor.

15. The cosmetic/dermatological composition as defined by claim 14, comprising from 0.0001% to 5% by weight of said phloroglucinol or of said at least one derivative thereof.

16. The cosmetic/dermatological composition as defined by claim 14, comprising from 0.001% to 2% by weight of said phloroglucinol or of said at least one derivative thereof.

17. The cosmetic/dermatological composition as defined by claim 14, further comprising an effective amount of at least one active species which stimulates the synthesis of collagen and/or the synthesis of lipids.

18. The cosmetic/dermatological composition as defined by claim 14 or 17, further comprising an effective amount of at least one hydrophilic or lipophilic gelling agent, hydrophilic or lipophilic active principle, preservative, antioxidant, solvent, fragrance, vitamin, filler, UV-screening agent, colorant, chelating agent and/or odor absorber.

19. The cosmetic/dermatological composition as defined by claim 14 or 17, further comprising an effective amount of at least one antibacterial agent, agent for combating parasites, antifungal agent, antiviral agent, anti-inflammatory agent, antipruriginous agent, anaesthetic agent, keratolytic agent, agent for combating free radicals, antiseborrhoeic agent, antidandruff agent, antiacne agent, agent which modulates cutaneous pigmentation and/or proliferation and/or differentiation, substance P, CGRP or bradykinin antagonist and/or NO-synthase inhibitor.

20. The cosmetic/dermatological composition as defined by claim 14 or 17, further comprising an effective amount of at least one calcium antagonist, OH radical scavenger, extract of Iridaceae or soybean, isoflavone, bacterial extract, potassium channel opener, spiroxazone, phospholipid, linoleic acid, linolenic acid, salicylic acid or derivative thereof, hydroxycarboxylic or ketocarboxylic acid or ester, lactone or salt thereof, anthralin, carotenoid, eicosatetraenoic or eicosatrienoic acid or ester or amide thereof, and/or vitamin D or derivative thereof.

21. The cosmetic/dermatological composition as defined by claim 14 or 17, formulated as a topically applicable aqueous, aqueous/alcoholic or oily solution, emulsion, gel, solid, paste, dispersion, cream, milk, lotion, serum, stick, or foam.

22. The cosmetic/dermatological composition as defined by claim 19, formulated as a topically applicable aqueous, aqueous/alcoholic or oily solution, emulsion, gel, solid, paste, dispersion, cream, milk, lotion, serum, stick, or foam.

* * * * *